United States Patent [19]

Petrocine et al.

[11] Patent Number: 4,477,679
[45] Date of Patent: Oct. 16, 1984

[54] PRODUCTION OF ALKYL-5-SUBSTITUTED-3-FUROATE COMPOUNDS

[75] Inventors: David V. Petrocine, Saddle River; John A. Swidinsky, Jackson, both of N.J.

[73] Assignee: CPC International Inc., Englewood Cliffs, N.J.

[21] Appl. No.: 471,082

[22] Filed: Mar. 1, 1983

[51] Int. Cl.³ .............................................. C07D 308/68
[52] U.S. Cl. ..................................... 549/486; 560/53; 560/60
[58] Field of Search ..................... 549/486; 560/53, 60

[56] References Cited

U.S. PATENT DOCUMENTS

| | | | |
|---|---|---|---|
| 2,421,223 | 5/1947 | Smith et al. | 167/24 |
| 2,772,198 | 11/1956 | Smith et al. | 167/24 |
| 3,393,990 | 7/1968 | Geary | 71/65 |
| 3,465,007 | 9/1969 | Elliott | 260/347.4 |
| 3,466,304 | 9/1969 | Elliott et al. | 549/488 X |
| 3,560,613 | 2/1971 | Miskus et al. | 424/174 |
| 3,567,744 | 3/1971 | Tanaka et al. | 549/486 X |
| 3,694,545 | 9/1972 | Roth et al. | 424/45 |
| 3,723,615 | 3/1973 | Okuno | 424/18 |
| 3,755,368 | 8/1973 | Huber | 260/340.9 |
| 3,792,079 | 2/1974 | D'Orazio | 260/468 |
| 3,796,730 | 3/1974 | Katsuda | 260/347.4 |
| 3,891,674 | 6/1975 | Diana et al. | 424/308 X |
| 4,037,352 | 7/1977 | Hennart et al. | 43/129 |
| 4,037,353 | 7/1977 | Hennart et al. | 43/129 |
| 4,056,610 | 11/1977 | Barber et al. | 424/32 |
| 4,094,969 | 6/1978 | Batzar | 424/78 |
| 4,190,680 | 2/1980 | Young et al. | 427/4 |
| 4,200,664 | 4/1980 | Young et al. | 427/4 |

FOREIGN PATENT DOCUMENTS

| | | |
|---|---|---|
| 2407403 | 10/1974 | Fed. Rep. of Germany . |
| 93529 | 9/1974 | Japan . |
| 47594 | 11/1975 | Japan . |
| 1429437 | 3/1976 | United Kingdom . |

OTHER PUBLICATIONS

Jones, JACS, vol. 77, (1955), p. 4069–4074.

Primary Examiner—Richard L. Raymond

[57] ABSTRACT

A process is disclosed for the production of alkyl-5-substituted-3-furoate compounds of the general formula:

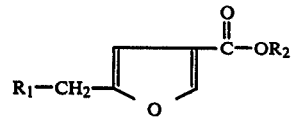

in which $R_1$ is an unsubstituted or substituted aryl which substituent will not affect the reaction, such as phenyl and $R_2$ is a lower alkyl having 1 to 6 carbon atoms employing alkyl-4-oxo-5-substituted-pentanoate as a starting material.

3 Claims, No Drawings

PRODUCTION OF ALKYL-5-SUBSTITUTED-3-FUROATE COMPOUNDS

SUMMARY OF THE PRESENT INVENTION

The present invention relates to a process for the production of alkyl-5-substituted-3-furoate compounds. In particular, the present invention relates to a process for the production of alkyl-5-substituted-3-furoate compounds of the general formula:

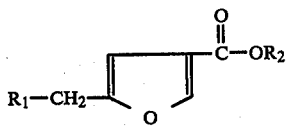

where $R_1$ is an unsubstituted or substituted aryl, which substituent will not affect the reaction described below, such as phenyl and $R_2$ is a lower alkyl having 1 to 6 carbon atoms, which method comprises:

(a) reacting a compound of the formula:

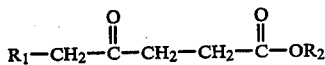

with an alkyl orthoformate under conditions which favor production of an enol ether of the formula:

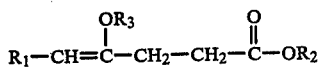

where $R_3$ represents the alkyl group of the alkyl orthoformate, (b) reacting the product of step (a) with sodium methoxide and an excess of carbon monoxide, to produce an alkyl-2-formyl-4-alkoxy-5-substituted pent-4-enoate represented as:

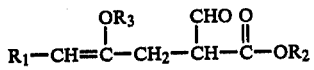

(c) reacting the product of step (b) with acid to provide an alkyl-5-substituted-3-furoate represented as:

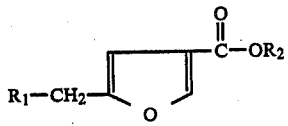

where $R_1$ is an unsubstituted or substituted aryl, which substituent will not affect the reaction, such as phenyl and $R_2$ is a lower alkyl having 1 to 6 carbon atoms.

BACKGROUND OF THE PRESENT INVENTION

A number of alkyl-5-substituted-3-furoate compounds of the kind provided by the process of the present invention are useful intermediates in the production of synthetic pyrethroid insecticides. In particular, ethyl-5-benzyl-3-furoate is a useful intermediate in the preparation of 5-benzyl-3-furyl methyl 2,2-dimethyl-3-(2-methylpropenyl)cyclopropanecarboxylate, a general purpose insecticide more commonly known by the generic name Resmethrin.

U.S. Pat. No. 3,465,007 to Elliott discloses many such synthetic pyrethroids modeled on the naturally occurring insecticide pyrethrum. The disclosed compounds are esters prepared by esterifying chrysanthemic acid or pyrethric acid with alcohols, such as 5-benzyl-3-furylmethyl alcohol.

U.S. Pat. No. 3,466,304, also to Elliott, discloses a method of preparing furan-substituted methanols by a complex synthesis, from a substituted-cyano compound condensed with an appropriate ester of succinic acid or succinic acid derivative.

U.S. Pat. No. 3,567,744 to Tanaka, et al., also shows a process for producing furoic acid derivatives. In addition to the claimed method which reacts 2-halo-5-halomethyl-3-furoic acid derivatives with an aromatic or heterocyclic compound, the reference details other methods then known to the art.

U.S. Pat. No. 3,755,368 to Huber shows a method for the preparation of 2-formyl esters involving the reaction of carboxylic compounds with carbon monoxide, preferably under pressure.

Japanese Pat. No. 137971/75 to Kondo and Matsui shows a method for the production of 5-benzyl-furan-3-carboxylic acid derivatives. The product compounds are the dehydrated condensation products of alpha-substituted hydrocinnamaldehydes and beta-keto acid esters.

The production methods in these references have all been more or less successful from a technical standpoint. However, problems with low yields, cost and availability of starting materials as well as the possibility of discovery of new and more effective pyrethroids have resulted in research into alternative synthesis.

OBJECTS OF THE PRESENT INVENTION

It is an object of the present invention to provide a synthesis for the preparation of pyrethroid precursors which may provide higher yields.

It is a further object of the present invention to provide a synthesis for the preparation of pyrethroid precursors which may utilize less costly and more readily available starting materials.

It is a still further object of the present invention to provide a synthesis for the preparation of pyrethroid precursors which may lead to the discovery of new and more effective pyrethroids.

The other objects, features and advantages of the present invention will become more apparent in light of the following detailed description of the preferred embodiment thereof.

According to the present invention, there is provided a process for the production of alkyl-5-substituted-3-furoate compounds of the general formula:

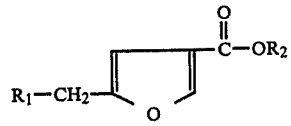

where $R_1$ is an unsubstituted or substituted aryl, which substituent will not affect the reaction, such as phenyl and $R_2$ is a lower alkyl having 1 to 6 carbon atoms, which method comprises:

(a) reacting a compound of the formula:

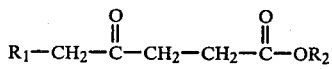

with an alkyl orthoformate under conditions which favor production of an enol ether of the formula:

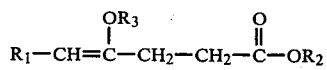

where $R_3$ represents the alkyl group of the alkyl orthoformate, (b) reacting the product of step (a) with sodium methoxide and an excess of carbon monoxide, to produce an alkyl-2-formyl-4-alkoxy-5-substituted pent-4-enoate represented as:

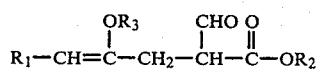

(c) reacting the product of step (b) with acid to provide an alkyl-5-substituted-3-furoate represented as:

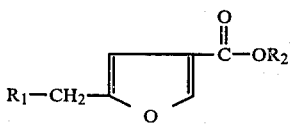

where $R_1$ is an unsubstituted or substituted aryl which substituent will not affect the reaction such as phenyl and $R_2$ is a lower alkyl having 1 to 6 carbon atoms.

DETAILED DESCRIPTION OF THE PRESENT INVENTION

It has now been found that an efficient and relatively specific synthesis of alkyl-5-substituted-3-furoate compounds can be obtained in the following manner. Utilizing as a starting material an alkyl-4-oxo-5-substituted pentanoate, an amount of that material is combined with an alkyl orthoformate in a suitable solvent. It is expected that both the di-alkoxy ketal and the enol ether will be formed and either could be isolated by suitable reaction conditions.

The enol ether thus prepared, an alkyl-4-alkoxy-5-substituted pent-4-enoate, is then reacted with sodium methoxide and an excess of carbon monoxide, to produce an alkyl-2-formyl-4-alkoxy-5-substituted pent-4-enoate. The procedure of this step is accomplished in the same manner as that employed in U.S. Pat. No. 3,755,368, having a common assignee, and the teachings of that reference are hereby incorporated by reference.

EXAMPLE

To a magnetically stirred 500 c.c. flask containing two-hundred cubic centimeters (200 c.c.) ethanol and two grams (2 g.) of a strong acidic resin cation, available commercially from the Dow Chemical Company under The trademark Dowex 50-W-X-3 ™, were added forty-four grams (44.0 g.) representing two-tenths of a mole (0.20 mole) of ethyl-4-oxo-5-phenyl pentanoate and thirty-seven grams (37.0 g.) representing twenty-five one-hundredths of a mole (0.25 mole) of ethyl orthoformate. The mixture was stirred at room temperature and periodic samples were taken to record the reaction's progress. Analysis by infrared spectrophotometry indicated that both the diethoxy ketal and the enol ether were formed, but as the reaction proceeded, conditions favored formation of the enol ether. The resin was removed by filtration and the product was vacuum distilled to yield forty-six and three-tenths gram (46.3 g.) of the enol ether.

The ethyl-4-ethoxy-5-phenyl pent-4-enoate formed in this manner was further reacted as follows. Twelve and four-tenths gram (12.4 g.) representing five one-hundredths of a mole (0.05 mole) of the enol ether were added to a standard PARR bottle, together with six and eight-tenths gram (6.8 g.) representing one-hundred and twenty-five one-hundredths of a mole (0.125 mole) of sodium methoxide and one-hundred and fifty milliliters (150 ml) toluene. The bottle was installed into a PARR shaker and flushed first with nitrogen and then with carbon monoxide. The pressure was increased to about 45-48 pounds per square inch gauge and the temperature was increased to between 60° C. and 65° C. After the reaction proceeded for two hours with make-up carbon monoxide being added as a necessary, the gelatinous sodium salt thus formed was acidified with eight and two-tenths milliliter (8.2 ml) glacial acetic acid and fifty milliliters (50 ml) water. The layers were allowed to separate and the organic layer was dried over sodium sulfate and then concentrated in vacuo to yield eleven and one-tenth gram (11.1 g.) of product.

The ethyl-2-formyl-4-ethoxy-5-phenyl pent-4-enoate formed in this manner was further reacted as follows. Eleven and one-tenth gram (11.1 g.) representing four one-hundredths of a mole (0.04 mole) of this material was added to a magnetically stirred flask, together with fifty-five grams (55 g.) of sulfuric acid, in a seventy-eight percent (78%) concentration in aqueous solution, and one-hundred and fifty millileters (150 ml) toluene. After allowing the mixture to react at room temperature for one and one-half hours (1½ hrs.) the layers were allowed to separate and the toluene layer was washed successively; first with twenty-five millileters (25 ml) water, then with twenty-five millileters (25 ml) saturated sodium bicarbonate and finally with another twenty-five millileters (25 ml) of water. The product thus obtained was then dried over sodium sulfate and concentrated in vacuo to yield seven and seven-tenths gram (7.7 g.) of product.

The product was confirmed to be ethyl 5-benzyl-3-furoate by both infrared spectrophotometry and nuclear magnetic reasonance spectroscopy.

What is claimed is:

1. A process for the production of alkyl-5-substituted-3-furoate compounds of the general formula

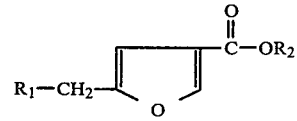

where $R_1$ is an unsubstituted or substituted aryl which substituent will not adversely affect the reaction, and $R_2$ is a lower alkyl having 1 to 6 carbon atoms, which method comprises (a) reacting a compound of the formula

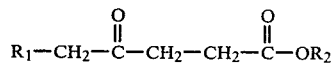

with an alkyl orthoformate under conditions which favor production of an enol ether of the formula

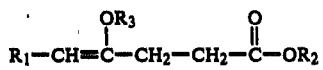

where $R_3$ represents the alkyl group of the alkyl orthoformate,
(b) reacting the product of step (a) with sodium methoxide and an excess of carbon monoxide, to produce an alkyl-2-formyl-4-alkoxy-5-substituted pent-4-enoate represented as

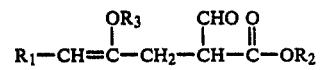

(c) reacting the product of step (b) with acid.
2. The process of claim 1 wherein $R_1$ is phenyl and $R_2$ is a lower alkyl having 1 to 6 carbon atoms.
3. The process of claim 2 wherein $R_2$ is ethyl.

* * * * *

UNITED STATES PATENT AND TRADEMARK OFFICE
CERTIFICATE OF CORRECTION

PATENT NO. : 4,477,679
DATED : October 16, 1984
INVENTOR(S) : David V. Petrocine and John A. Swidinsky It is certified that error appears in the above-identified patent and that said Letters Patent are hereby corrected as shown below:

On the title page;

Cover Sheet, Assignee, "CPC International Inc., Englewood Cliffs, N.J." should be--Penick Corporation, Lyndhurst, N.J.--.

Signed and Sealed this

Twenty-fifth Day of June 1985

[SEAL]

Attest:

DONALD J. QUIGG

Attesting Officer

Acting Commissioner of Patents and Trademarks